US00PP32350P2

(12) United States Plant Patent
Wells

(10) Patent No.: US PP32,350 P2
(45) Date of Patent: Oct. 20, 2020

(54) ***PINUS* TREE NAMED 'MONJAW'**

(50) Latin Name: *Pinus mugo*
Varietal Denomination: MonJaw

(71) Applicant: Richard Wells, McMinniville, OR (US)

(72) Inventor: Richard Wells, McMinniville, OR (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 16/602,314

(22) Filed: Sep. 10, 2019

(51) Int. Cl.
*A01H 7/00* (2006.01)

(52) U.S. Cl.
USPC ..... Plt./213

(58) Field of Classification Search
USPC ..... Plt./213
CPC ... A01H 7/00; A01H 5/00; A01H 5/04; A01H 5/02; A01H 5/025
See application file for complete search history.

*Primary Examiner* — June Hwu
(74) *Attorney, Agent, or Firm* — Cassandra Bright

(57) ABSTRACT

A new and distinct cultivar of *Pinus mugo* named 'MonJaw' is disclosed, characterized by its compact, mounding form, bright green winter color, and long needles. The new cultivar is a *Pinus*, typically suited for ornamental use.

2 Drawing Sheets

Latin name of the genus and species: *Pinus mugo*.
Variety denomination: 'MonJaw'.

BACKGROUND OF THE INVENTION

The new cultivar is a chance discovery in an existing population of the unpatented variety *Pinus mugo* 'Pumilo' seedlings, by the inventor Richard Wells. This discovery was made in a seedling bed at a commercial nursery in Dayton Oreg. in Spring 2012.

Asexual reproduction was first performed by grating terminal vegetative scions onto unnamed, *Pinus mugo* seedling rootstock in December 2012, at the same nursery in Dayton, Oreg. Subsequently trials with ungrafted rooted cuttings began in 2014. 'MonJaw' has since produced additional generations and has shown that the unique features of this cultivar are stable and reproduced true to type.

SUMMARY OF THE INVENTION

The cultivar 'MonJaw' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MonJaw'. These characteristics in combination distinguish 'MonJaw' as a new and distinct *Pinus* cultivar:

1. Medium sized plant growing to about 4'×4' at maturity.
2. Compact growth with mounding form.
3. Maintains a bright green color throughout winter.
4. Developing candles have an attractive brownish coloration during late winter/early spring; especially the base of the candles.
5. Needle length is 2-2.5 inches.

PARENTAL COMPARISON

Plants of the new cultivar 'MonJaw' are similar to the parent variety *Pinus mugo* 'Pumilo', unpatented, in most horticultural characteristics. However, plants of 'MonJaw' differ in the following ways:

1. New variety has a more compact, mounding form than the parent variety.
2. New variety maintains a more consistent green winter color than the parent variety.

COMMERCIAL COMPARISON

Plants of the new cultivar 'MonJaw' are similar to the unpatented variety *Pinus mugo* 'Sherwood Compact' in most horticultural characteristics; however, plants of 'MonJaw' differ in the following ways:

1. 'MonJaw' is a larger plant than 'Sherwood Compact'.
2. New variety has larger, brownish candles, while this comparator has smaller, whitish candles.
3. New variety has longer needles than this comparator.
4. Comparator is lower growing and more spreading than 'MonJaw'.
5. New variety maintains a bright green color throughout winter, while this comparator has significant yellowing in the winter.

Plants of the new cultivar 'MonJaw' are also similar to the unpatented variety *Pinus mugo* 'Slowmound' in most horticultural characteristics; however, plants of 'MonJaw' differ in the following ways:

1. 'MonJaw' is a larger plant than 'Slowmound'.
2. New variety has brownish candles, while this comparator has whitish candles.
3. New variety has longer needles than this comparator.

BRIEF DESCRIPTION OF THE PHOTOGRAPHS

Figure 1:
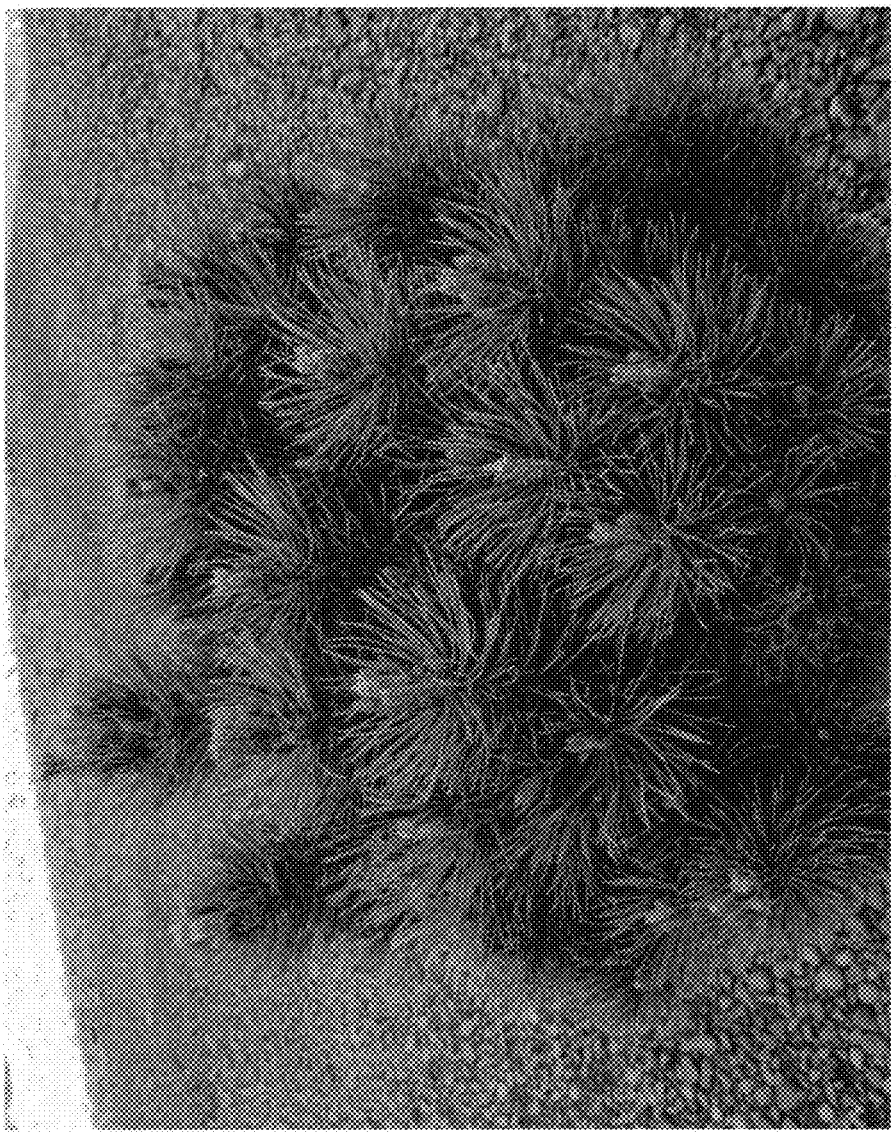

The accompanying photograph in FIG. 1 illustrates in full color a typical plant of 'MonJaw' grown outdoors in Dayton, Oreg. This plant is approximately 4 years old.

Figure 2:
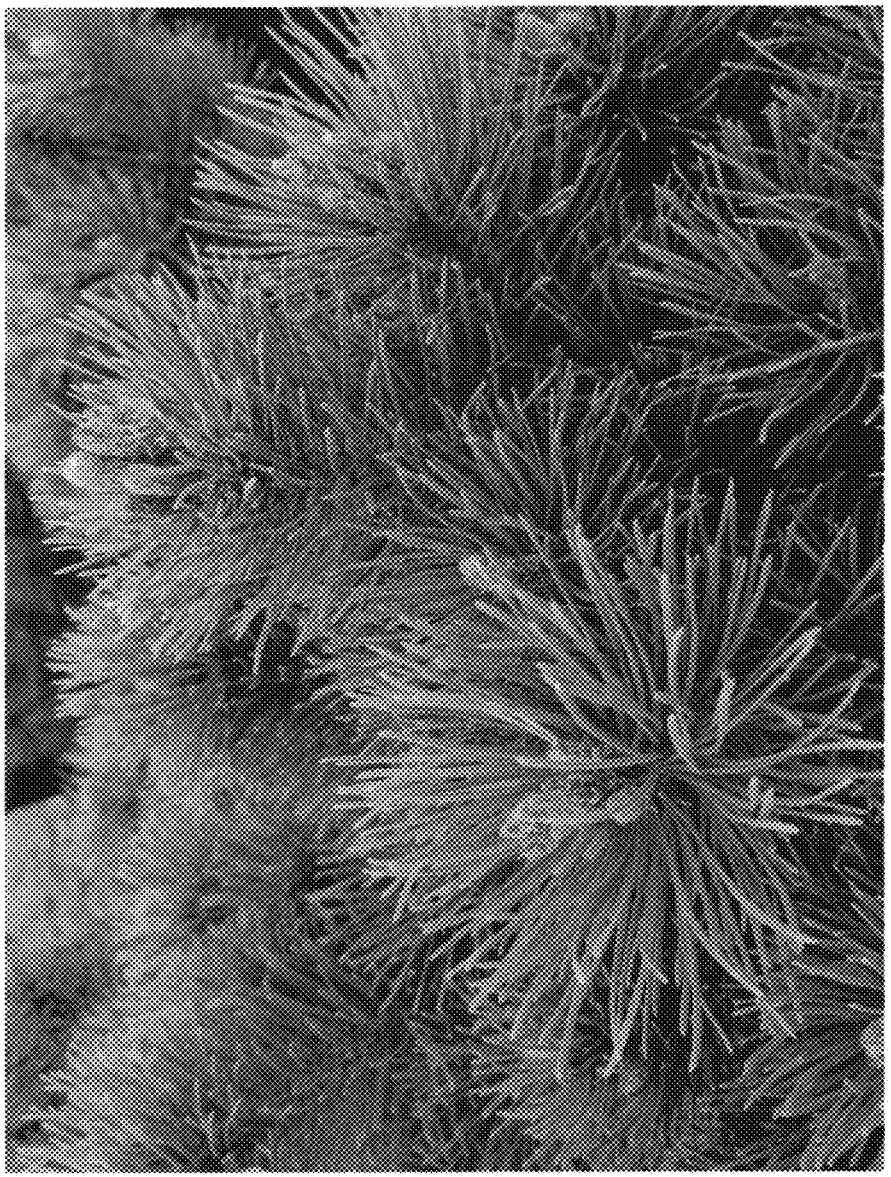

FIG. 2 illustrates a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 except where general terms of ordinary dictionary significance are used. The following observations and measurements describe 'MonJaw' plants grown outdoors in Dayton, Oreg. Unless noted as values taken from a mature plant, values are taken from a plant approximately 4 years old, grown in a 3 liter pot. The plant has been grafted onto a seedling of *Pinus mugo*. The specimen is approximately 4 years old, grown outdoors in Dayton, Oreg. No artificial light, photoperiodic treatments or chemical treatments were given to the plants. Measurements and numerical values represent averages of typical plant types.

Botanical classification: *Pinus mugo* 'MonJaw'.

Age of the plant described: Values are taken from a 4-year-old specimen, unless noted as a mature tree measurement.

Container size of the plant described: 3 gallon commercial container.

PROPAGATION

Time to rooting: 60 to 90 days at approximately 40°-50° F.

Root description: Woody main roots, colored near RHS Brown 200D. Lateral roots fibrous, very well branched, colored near RHS Grey-Brown 199A.

PLANT

Growth habit: Globular, low growing dwarf tree.

Height: Approximately 35 cm.

Plant spread: Approximately 45 cm.

Typical growth rate: Moderate for species.

Pinching required: No.

Branching characteristics: Single main stem with approximately 15 to 20 lateral branches emerging very low to soil line (about 3 cm). Lateral stems have a slight curve, rather than acute angle at the point of attachment. The angle from the main stem is approximately 45 to 80° from the center of the plant. Main lateral branches split into 3 to 4 secondary branches.

Length of lateral branches: Average 6 to 10 cm before splitting into secondary branches.

Diameter of lateral branches: Average 9 to 15 mm.

Lateral branch shape in cross section: Round.

Lateral branch strength: Very strong, moderately flexible.

Lateral branch color: Near RHS Brown 200B.

Lateral branch texture: Very rough, scaly.

Internode length: Average range between 1.0 and 2.0 cm.

Bark: Scaly, colored near RHS Brown 200B and Grey-Brown N199A.

Candles/new growth:

*Length*.—Average range between 5 to 8 cm.

*Diameter*.—Average 1.8 cm.

*Shape*.—Cylindric.

*Color*.—Near Greyed-Orange 175A, apical section Grey-Brown 199D.

FOLIAGE

General description: Needles, held 2 per group.

Leaf:

*Arrangement*.—Radially arranged fascicles, 2 needles per fascicle.

*Type*.—Needle.

*Shape of blade*.—Needle.

*Average length*.—Approximately 6.5 cm.

*Average width*.—Approximately 1 mm.

*Apex*.—Acute, not very sharp.

*Base*.—Sessile.

*Fascicle sheath*.—Length: 4 to 5 mm. Width: 2 mm. Color: Near RHS Brown 200B.

*Attachment*.—Sessile.

*Margin*.—Entire.

*Aspect*.—Straight to very slightly curved.

*Texture of top surface*.—Glabrous.

*Texture of bottom surface*.—Glabrous.

*Fascicle internode length*.—Approximately 2 mm.

*Color*.—Young foliage upper side: Near RHS Green 137C. Young foliage under side: Near RHS Green 137C. Mature foliage upper side: Near RHS Green 137C. Mature foliage under side: Near RHS Green 137C. Winter foliage upper side: Near RHS Green 137C. Winter foliage under side: Near RHS Green 137C.

*Venation*.—Linear, indistinguishable from leaf blade.

*Fragrance*.—Faint to mild pine scent.

FLOWER

Flowering not observed.

REPRODUCTIVE ORGANS

General description of visible parts: Not observed.

OTHER CHARACTERISTICS

Cone: Not observed.

Drought tolerance and temperature tolerance: Low temperature tolerance to approximately −40° C. Tolerates high temperature to at least 30° C. Moderate drought tolerance.

Disease/pest resistance: Neither extra resistance nor susceptibility to the normal pests and diseases of *Pinus* has been observed.

What is claimed is:

1. A new and distinct cultivar of *Pinus mugo* tree named 'MonJaw' as herein illustrated and described.

* * * * *